United States Patent
Oskin et al.

(10) Patent No.: US 11,504,541 B2
(45) Date of Patent: Nov. 22, 2022

(54) WEARABLE THERAPEUTIC DEVICE

(71) Applicant: ZOLL MEDICAL CORPORATION, Chelmsford, MA (US)

(72) Inventors: Emil Oskin, Natrona Heights, PA (US);
Philip C. Skalos, Munhall, PA (US);
Thomas E. Kaib, Irwin, PA (US)

(73) Assignee: ZOLL MEDICAL CORPORATION, Chelmsford, MA (US)

(*) Notice: Subject to any disclaimer, the term of this patent is extended or adjusted under 35 U.S.C. 154(b) by 0 days.

(21) Appl. No.: 17/143,376

(22) Filed: Jan. 7, 2021

(65) Prior Publication Data

US 2021/0128930 A1 May 6, 2021

Related U.S. Application Data

(63) Continuation of application No. 16/751,466, filed on Jan. 24, 2020, now Pat. No. 10,926,098, which is a
(Continued)

(51) Int. Cl.
*A61N 1/39* (2006.01)
*A61B 5/318* (2021.01)
(Continued)

(52) U.S. Cl.
CPC ............ *A61N 1/3918* (2013.01); *A61B 5/318* (2021.01); *A61B 5/6804* (2013.01); *A61N 1/04* (2013.01);
(Continued)

(58) Field of Classification Search
CPC ...... A61N 1/3918; A61N 1/04; A61N 1/0484; A61N 1/3968; A61N 1/3993; A61B 5/318; A61B 5/6804
See application file for complete search history.

(56) References Cited

U.S. PATENT DOCUMENTS 3,991,747 A 11/1976 Stanly et al.
4,016,868 A 4/1977 Allison
(Continued)

FOREIGN PATENT DOCUMENTS

DE 2644236 C3 4/1981
EP 0295497 B1 9/1993
(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/full/166/1/111.
(Continued)

*Primary Examiner* — Ryan W Sherwin
(74) *Attorney, Agent, or Firm* — Lando & Anastasi, LLP

(57) ABSTRACT

A wearable therapeutic device is provided. The wearable therapeutic device includes a garment, and the garment includes an electrode and a conductive thread. A control unit is coupled to the conductive thread and identifies an electrical connection between a conductive surface of the electrode and the conductive thread, and an alarm module can provide information about the positioning of the electrode in the garment based on the electrical connection.

20 Claims, 6 Drawing Sheets

Related U.S. Application Data continuation of application No. 16/257,854, filed on Jan. 25, 2019, now Pat. No. 10,589,110, which is a continuation of application No. 14/630,947, filed on Feb. 25, 2015, now Pat. No. 10,226,638, which is a continuation of application No. 13/315,894, filed on Dec. 9, 2011, now Pat. No. 9,007,216.

(60) Provisional application No. 61/530,585, filed on Sep. 2, 2011, provisional application No. 61/421,970, filed on Dec. 10, 2010.

(51) Int. Cl.
*A61N 1/04* (2006.01)
*A61B 5/00* (2006.01)

(52) U.S. Cl.
CPC ......... *A61N 1/0484* (2013.01); *A61N 1/3968* (2013.01); *A61N 1/3993* (2013.01)

(56) References Cited

U.S. PATENT DOCUMENTS

| | | | |
|---|---|---|---|
| 4,094,310 A | 6/1978 | McEachern et al. | |
| 4,576,170 A | 3/1986 | Bradley et al. | |
| 4,632,122 A | 12/1986 | Johansson et al. | |
| 4,763,660 A | 8/1988 | Kroll et al. | |
| 4,827,943 A | 5/1989 | Bornn et al. | |
| 4,928,690 A | 5/1990 | Heilman et al. | |
| 4,978,926 A | 12/1990 | Zerod et al. | |
| 5,007,427 A | 4/1991 | Suzuki et al. | |
| 5,062,834 A | 11/1991 | Gross et al. | |
| 5,078,134 A | 1/1992 | Heilman et al. | |
| 5,348,008 A | 9/1994 | Bornn et al. | |
| 5,365,932 A | 11/1994 | Greenhut | |
| 5,454,376 A | 10/1995 | Stephens et al. | |
| 5,472,453 A | 12/1995 | Alt | |
| 5,662,689 A | 9/1997 | Elsberry et al. | |
| 5,718,242 A | 2/1998 | McClure et al. | |
| 5,738,102 A | 4/1998 | Lemelson | |
| 5,741,306 A | 4/1998 | Glegyak et al. | |
| 5,758,443 A | 6/1998 | Pedrazzini | |
| 5,792,190 A | 8/1998 | Olson et al. | |
| 5,929,601 A | 7/1999 | Kaib et al. | |
| 5,944,669 A | 8/1999 | Kaib | |
| 6,016,445 A | 1/2000 | Baura | |
| 6,047,203 A | 4/2000 | Sackner et al. | |
| 6,065,154 A * | 5/2000 | Hulings | A61N 1/3904 2/102 |
| 6,097,982 A | 8/2000 | Glegyak et al. | |
| 6,097,987 A | 8/2000 | Milani | |
| 6,169,397 B1 | 1/2001 | Steinbach et al. | |
| 6,253,099 B1 | 6/2001 | Oskin et al. | |
| 6,272,365 B1 | 8/2001 | Ronkainen et al. | |
| 6,280,461 B1 | 8/2001 | Glegyak et al. | |
| 6,390,996 B1 | 5/2002 | Halperin et al. | |
| 6,561,975 B1 | 5/2003 | Pool et al. | |
| 6,681,003 B2 | 1/2004 | Linder et al. | |
| 6,690,969 B2 | 2/2004 | Bystrom et al. | |
| 6,804,554 B2 | 10/2004 | Ujhelyi et al. | |
| 6,827,695 B2 | 12/2004 | Palazzolo et al. | |
| 6,908,437 B2 | 6/2005 | Bardy | |
| 6,990,373 B2 | 1/2006 | Jayne et al. | |
| 7,089,054 B2 | 8/2006 | Palti | |
| 7,149,579 B1 | 12/2006 | Koh et al. | |
| 7,158,822 B2 | 1/2007 | Payne, Jr. | |
| 7,220,235 B2 | 5/2007 | Geheb et al. | |
| 7,340,296 B2 | 3/2008 | Stahmann et al. | |
| 7,453,354 B2 | 11/2008 | Reiter et al. | |
| 7,488,293 B2 | 2/2009 | Marcovecchio et al. | |
| 7,831,303 B2 | 11/2010 | Rueter et al. | |
| 7,974,689 B2 | 7/2011 | Volpe et al. | |
| 8,094,009 B2 | 1/2012 | Allen et al. | |
| 8,121,683 B2 | 2/2012 | Bucher et al. | |
| 8,140,154 B2 | 3/2012 | Donnelly et al. | |
| 8,271,082 B2 | 9/2012 | Donnelly et al. | |
| 8,494,658 B2 | 7/2013 | Crowe et al. | |
| 8,738,137 B2 | 5/2014 | Dar et al. | |
| 8,868,216 B2 | 10/2014 | Dunagan | |
| 9,007,216 B2 | 4/2015 | Oskin et al. | |
| 10,226,638 B2 | 3/2019 | Oskin et al. | |
| 10,589,110 B2 | 3/2020 | Oskin et al. | |
| 2003/0004547 A1 | 1/2003 | Owen et al. | |
| 2003/0095648 A1 | 5/2003 | Kaib et al. | |
| 2003/0149462 A1 | 8/2003 | White et al. | |
| 2003/0158593 A1 | 8/2003 | Heilman et al. | |
| 2003/0174049 A1 | 9/2003 | Beigel et al. | |
| 2003/0195567 A1 | 10/2003 | Jayne et al. | |
| 2003/0212311 A1 | 11/2003 | Nova et al. | |
| 2005/0049515 A1 | 3/2005 | Misczynski et al. | |
| 2005/0131465 A1 | 6/2005 | Freeman et al. | |
| 2006/0036292 A1 | 2/2006 | Smith et al. | |
| 2006/0085049 A1 | 4/2006 | Cory et al. | |
| 2006/0211934 A1 | 9/2006 | Hassonjee et al. | |
| 2006/0270952 A1 | 11/2006 | Freeman et al. | |
| 2007/0118056 A1 | 5/2007 | Wang et al. | |
| 2007/0161913 A1 | 7/2007 | Farrell et al. | |
| 2007/0169364 A1 | 7/2007 | Townsend et al. | |
| 2007/0239220 A1 | 10/2007 | Greenhut et al. | |
| 2007/0255347 A1 * | 11/2007 | Torgerson | A61N 1/3605 607/59 |
| 2007/0265671 A1 | 11/2007 | Roberts et al. | |
| 2008/0004536 A1 | 1/2008 | Baxi et al. | |
| 2008/0030656 A1 | 2/2008 | Watson et al. | |
| 2008/0033495 A1 | 2/2008 | Kumar | |
| 2008/0045815 A1 | 2/2008 | Derchak et al. | |
| 2008/0046015 A1 | 2/2008 | Freeman et al. | |
| 2008/0058658 A1 | 3/2008 | Noguchi | |
| 2008/0058884 A1 | 3/2008 | Matos | |
| 2008/0200792 A1 * | 8/2008 | Schmidt | A61B 5/6831 600/388 |
| 2008/0249591 A1 | 10/2008 | Gaw et al. | |
| 2008/0306560 A1 | 12/2008 | Macho et al. | |
| 2008/0306562 A1 | 12/2008 | Donnelly et al. | |
| 2008/0312520 A1 | 12/2008 | Rowlandson et al. | |
| 2008/0312522 A1 | 12/2008 | Rowlandson et al. | |
| 2009/0073991 A1 | 3/2009 | Landrum et al. | |
| 2009/0076336 A1 | 3/2009 | Mazar et al. | |
| 2009/0076340 A1 | 3/2009 | Libbus et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076344 A1 | 3/2009 | Libbus et al. | |
| 2009/0076345 A1 | 3/2009 | Manicka et al. | |
| 2009/0076346 A1 | 3/2009 | James et al. | |
| 2009/0076348 A1 | 3/2009 | Manicka et al. | |
| 2009/0076349 A1 | 3/2009 | Libbus et al. | |
| 2009/0076350 A1 | 3/2009 | Bly et al. | |
| 2009/0076363 A1 | 3/2009 | Bly et al. | |
| 2009/0076364 A1 | 3/2009 | Libbus et al. | |
| 2009/0076397 A1 | 3/2009 | Libbus et al. | |
| 2009/0076405 A1 | 3/2009 | Amurthur et al. | |
| 2009/0076410 A1 | 3/2009 | Libbus et al. | |
| 2009/0076559 A1 | 3/2009 | Libbus et al. | |
| 2009/0082831 A1 * | 3/2009 | Paul | A61N 1/0472 607/59 |
| 2009/0088652 A1 | 4/2009 | Tremblay | |
| 2009/0093687 A1 | 4/2009 | Telfort et al. | |
| 2009/0138059 A1 | 5/2009 | Ouwerkerk | |
| 2009/0234410 A1 | 9/2009 | Libbus et al. | |
| 2009/0264792 A1 | 10/2009 | Mazar | |
| 2009/0275848 A1 | 11/2009 | Brockway et al. | |
| 2009/0287120 A1 | 11/2009 | Ferren et al. | |
| 2009/0292194 A1 | 11/2009 | Libbus et al. | |
| 2010/0052898 A1 | 3/2010 | Allen et al. | |
| 2010/0056881 A1 | 3/2010 | Libbus et al. | |
| 2010/0069735 A1 | 3/2010 | Berkner | |
| 2010/0076513 A1 | 3/2010 | Warren et al. | |
| 2010/0076533 A1 | 3/2010 | Dar et al. | |
| 2010/0081962 A1 | 4/2010 | Hamaguchi et al. | |
| 2010/0234716 A1 | 9/2010 | Engel | |
| 2010/0234908 A1 * | 9/2010 | Didon | A61N 1/3968 607/5 |
| 2010/0298899 A1 | 11/2010 | Donnelly et al. | |

(56) References Cited

U.S. PATENT DOCUMENTS

| | | |
|---|---|---|
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0123232 A1 | 5/2012 | Najarian et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2020/0230429 A1 | 7/2020 | Oskin et al. |

FOREIGN PATENT DOCUMENTS

| | | |
|---|---|---|
| EP | 0335356 B1 | 3/1996 |
| EP | 1455640 B1 | 1/2008 |
| EP | 1720446 B1 | 7/2010 |
| JP | 5115450 A | 5/1993 |
| WO | 200002484 A1 | 1/2000 |
| WO | 2004054656 A1 | 7/2004 |
| WO | 2009137683 A2 | 11/2009 |

OTHER PUBLICATIONS

DeBock, et al., "Captopril treatment of chronic heart failure in the very old," J. Gerontol. (1994) 49: M148-M152.

International Search Report from corresponding PCT Application No. US2011064056 dated Apr. 4, 2012.

O'Keeffe et al., "Reproducability and responsiveness of quality of life assessment and six minute walk test in elderly heart failure patients," Heart (1998) 80: 377-382.

Office Action from corresponding Japanese Application No. 2013-543364 dated Oct. 13, 2015.

\* cited by examiner

WEARABLE THERAPEUTIC DEVICE

CROSS-REFERENCE TO RELATED APPLICATIONS

This application claims the benefit under 35 U.S.C. § 120 as a continuation of U.S. application Ser. No. 16/751,466, titled "WEARABLE THERAPEUTIC DEVICE," filed Jan. 24, 2020, which claims the benefit under 35 U.S.C. § 120 as a continuation of U.S. application Ser. No. 16/257,854, titled "WEARABLE THERAPEUTIC DEVICE," filed Jan. 25, 2019, now U.S. Pat. No. 10,589,110, which claims the benefit under 35 U.S.C. § 120 as a continuation of U.S. application Ser. No. 14/630,947, titled "WEARABLE THERAPEUTIC DEVICE," filed Feb. 25, 2015, now U.S. Pat. No. 10,226,638, which claims the benefit under 35 U.S.C. § 120 as a continuation of U.S. application Ser. No. 13/315,894, titled "WEARABLE THERAPEUTIC DEVICE," filed Dec. 9, 2011, now U.S. Pat. No. 9,007,216, which claims priority under 35 U.S.C. § 119(e) to U.S. Provisional Application Ser. No. 61/421,970 titled "WEARABLE THERAPEUTIC DEVICE," filed Dec. 10, 2010 and to U.S. Provisional Application Ser. No. 61/530,585 titled "WEARABLE THERAPEUTIC DEVICE," filed Sep. 2, 2011, each of which is incorporated herein by reference in its entirety.

BACKGROUND OF THE INVENTION

1. Field of the Invention

At least one embodiment of the present invention relates generally to a wearable therapeutic device, and more specifically, to a wearable therapeutic device having electrodes configured to monitor or treat a subject.

2. Discussion of the Related Art

Cardiac arrest and other health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival. Health care professionals also attempt to detect and prevent conditions conducive to cardiac ailments by treating patients with drugs or by suggesting lifestyle changes. These efforts are expensive and have a limited success rate, and cardiac arrest, among other conditions, continues to claim the lives of victims.

SUMMARY OF THE INVENTION

Aspects and embodiments of the present invention are directed to a wearable therapeutic device that is configured to be worn by a subject. The wearable therapeutic device includes at least one electrode in, for example, a pocket of the wearable therapeutic device. When properly positioned, a conductive surface of the electrode can be disposed in the pocket to face the subject, proximate to the subject's skin so that information (e.g., cardiac information) can be sensed or treatment (e.g., a defibrillation shock) can be applied to the subject. A conductive thread can be sewn into parts of the wearable therapeutic device, including parts of the pocket that are not proximate to the subject's skin. A circuit can be formed when the conductive surface of the electrode couples with the conductive thread. When this circuit is formed, the conductive surface of the electrode is generally not proximate to the subject's skin, and not in position to apply treatment. Based on the coupling of the conductive surface of the electrode and the conductive thread, an alarm module can indicate that the electrode is or is not properly positioned.

At least one aspect is directed to a wearable therapeutic device. The wearable therapeutic device includes a garment, and the garment includes an electrode and a conductive thread. A control unit is coupled to the conductive thread and identifies an electrical connection between a conductive surface of the electrode and the conductive thread, and an alarm module indicates information about the positioning of the electrode in the garment based on the electrical connection.

At least one other aspect is directed to a method of facilitating care of a subject. The method provides a wearable therapeutic device that includes an electrode and a conductive thread. The method also identifies an electrical connection between a conductive surface of the electrode and the conductive thread. The method provides a notification to indicate positioning information of the electrode based on the electrical connection.

At least one other aspect is directed to and method that includes providing a wearable therapeutic device including a garment. The garment houses an electrode and includes conductive thread. The wearable therapeutic device includes a control unit coupled to the conductive thread. The control unit identifies an electrical connection between the electrode and the conductive thread. An alarm module indicates positioning information of the electrode in the garment based on the electrical connection.

The electrode can be a therapy electrode or a sensing electrode. In some embodiments, the garment includes a pocket that houses the electrode. The pocket can have a first lateral side and a second lateral side, with the conductive thread sewn into the first lateral side or into the second lateral side. In one embodiment, one lateral side includes a conductive mesh and the other includes the conductive thread. The first lateral side can be proximate to a subject, and the second lateral side can be distal to the subject, with the conductive thread disposed in the second lateral side of the pocket.

In one embodiment, a conductive element can be included in the garment. A connector can couple the conductive thread with the conductive element. The control unit is further can detect a current path that includes the conductive thread, the conductive surface of the electrode, and the conductive element. In one embodiment, the garment includes a belt, with a conductive element included in the belt. A connector can couple the conductive thread with the conductive element to form electrical connection between the conductive surface of the electrode and the conductive element. The connector may include a snap. The conductive element can connect with the conductive thread at one or more points of the conductive thread.

In one embodiment, the conductive thread forms a stitched pattern in the garment. The conductive thread can also form a stitched pattern including at least two substantially parallel stitched lines, or a pattern in at least one of a quadrilateral shape, a polygonal shape, an oblong shape, a circular shape, an oval shape, a round shape, and a triangular shape. In one embodiment, the conductive thread forms part of an electrical connection with the electrode.

In one embodiment, the alarm module can notify a subject wearing the wearable therapeutic device, or a health care provider, that the electrode is properly or improperly positioned. A monitor can display an indication that the electrode is properly or improperly positioned.

In some embodiments, the electrode can be housed in a pocket of the garment, and the conductive thread can be woven into the pocket. The electrode can be determined to be positioned with a conductive surface facing away from a subject. A closed circuit that includes a conductive surface of the electrode and the conductive thread can be detected, and improper positioning of the electrode can be determined. In one embodiment, the wearable therapeutic device includes a conductive element, and a current path that includes the conductive thread, the conductive surface of the electrode, and the conductive element can be detected. In one embodiment, the conductive thread can be coupled with the conductive element.

In one embodiment, instructions can be provided to operate the wearable therapeutic device. The instructions can include at least one instruction directing a subject to position a conductive surface of the electrode proximate to the subject. The wearable therapeutic device can include a garment with a pocket to house the electrode. The pocket can be formed at least in part from a conductive mesh, and instructions can be provided to position a conductive surface of the electrode facing the conductive mesh. Instructions can also be provided to position a conductive surface of the electrode facing away from the conductive thread.

Other aspects and embodiments are discussed in detail below. The foregoing information and the following detailed description include illustrative examples of various aspects and embodiments, and are intended to provide an overview or framework for understanding the nature and character of the claimed aspects and embodiments. The drawings provide illustration and a further understanding of the various aspects and embodiments, and are incorporated in and constitute a part of this specification. The drawings, together with the remainder of the specification, serve to describe and explain the claimed aspects and embodiments.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
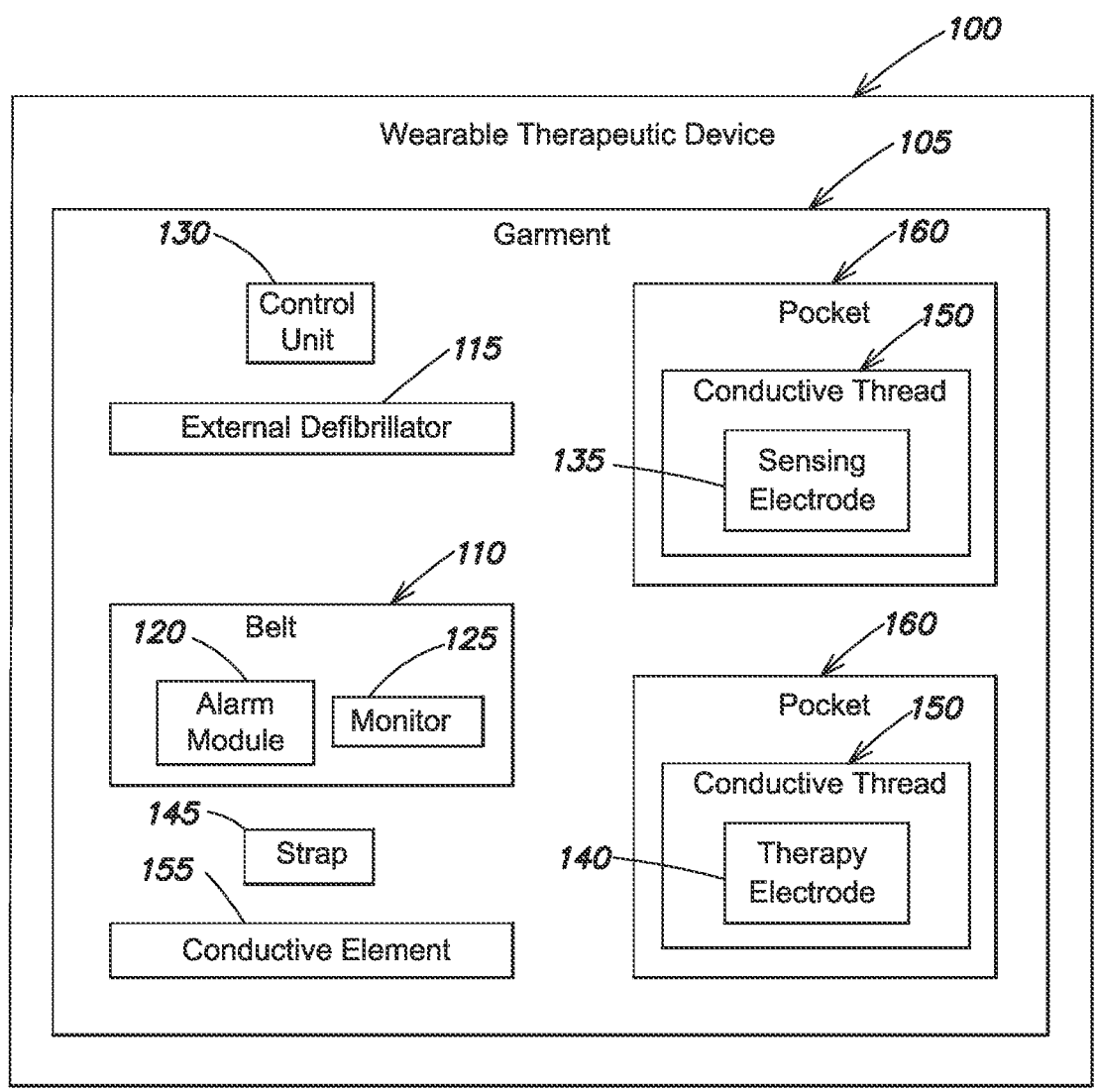
FIG. 1 is a block diagram depicting a wearable therapeutic device in accordance with an embodiment.

The systems and methods described herein are not limited in their application to the details of construction and the arrangement of components set forth in the description or illustrated in the drawings. The invention is capable of other embodiments and of being practiced or of being carried out in various ways. Also, the phraseology and terminology used herein is for the purpose of description and should not be regarded as limiting. The use of "including" "comprising" "having" "containing" "involving" and variations thereof herein, is meant to encompass the items listed thereafter, equivalents thereof, and additional items, as well as alternate embodiments consisting of the items listed thereafter exclusively.

Various aspects and embodiments are directed to a wearable therapeutic device that can be worn by a subject. The wearable therapeutic device can include a garment with at least one pocket to house at least one electrode. When the electrode is properly positioned, a conductive surface of the electrode faces the subject and directly or indirectly contacts the subject's skin. When properly positioned, the electrode can apply therapy, such as a defibrillation shock, to the subject. Due, for example, to subject motion or improper installation by the subject, a health care provider or manufacturer, the electrode can become improperly positioned, so that its conductive surface does not face the subject. When the electrode is improperly positioned, its conductive surface can contact a conductive thread included in the garment. This can form an electrical connection, and detection of this electrical connection can indicate that the electrode is improperly positioned to sense information about or apply therapy to the subject. An alarm module can provide a notification that the electrode is properly or improperly positioned. Corrective action can be taken to properly position the electrode.

FIG. 1 is a block diagram of wearable therapeutic device 100 in accordance with an embodiment. In one embodiment, wearable therapeutic device 100 includes the wearable therapeutic device described in commonly owned U.S. patent application Ser. No. 13/109,079, titled "Wearable Therapeutic Device," filed on May 17, 2011, which is incorporated by reference herein in its entirety. The referenced application generally describes a wearable therapeutic device.

Wearable therapeutic device 100 can include at least one garment 105 in the shape of a vest or shirt. Garment 105 may also include at least one belt 110. Belt 110 may be worn about a subject's waist, at a higher location about or across the subject's chest, or at other locations between the subject's waist and shoulders. Components of wearable therapeutic device 100, including garment 105, can be worn under, over, or partially under and partially over a subject's clothes. In one embodiment, garment 105 is formed from breathable fabric. Garment 105 may also be stretchable.

In one embodiment, wearable therapeutic device 100 includes at least one of the following elements: garment 105, belt 110, external defibrillator 115, alarm module 120, monitor 125, control unit 130, sensing electrode 135, therapy electrode 140, strap 145, conductive thread 150, conductive element 155, and pocket 160. In one embodiment, at least one of external defibrillator 115, alarm module 120, monitor 125, control unit 130, sensing electrode 135, therapy electrode 140, conductive thread 150, conductive element 155, and pocket 160 are included in or attached to garment 105, belt 110 or strap 145. For example, wearable therapeutic device 100 components can be fitted into open or closed pockets 160, or otherwise attached to garment 105 via buckles, hook and loop fasteners, holsters, loops, pouches or sleeves that form part of belt 110 or strap 145. These elements may also be integrated into belt 110 or strap 145, and these elements may be a permanent part of belt 110 or strap 145, or releasable from belt 110 or strap 145. Garment 105 may include a series of belts 110 or straps 145, and need not constitute an article of clothing. Wearable therapeutic device 100 may include one, more than one, or all of the above mentioned elements, as well as additional elements such as at least one power supply to provide power to control unit 130, external defibrillator 115, alarm module 120, monitor 125, sensing electrodes 135, or therapy electrodes 140.

External defibrillator 115 can be included as part of wearable therapeutic device 100. For example, external defibrillator 115 can be included in garment 105, pocket 160, attached to strap 145, or disposed in belt 110. In one embodiment, external defibrillator 115 is electrically coupled to therapy electrode 140. Wearable therapeutic device 100 may include at least one receptacle having a conductive fluid encapsulated therein and housed in garment 105. For example, the receptacle can be disposed in belt 110 or strap 145, proximate to at least one of sensing electrode 135 and therapy electrode 140. In one embodiment, electrodes 135 and 140 are dry electrodes. Control unit 130 can release the conductive fluid from the receptacles to enhance an electrical connection between sensing electrode 135 or therapy electrode 140 and a subject wearing wearable therapeutic device 100 to, for example, sense electrocardiograph information about the subject or to apply treatment to the subject. The receptacles can be replaced after their conductive fluid has been released, or upon their expiration. When a shock is applied, therapy electrodes 140, the subject's body, and external defibrillator 115 form at least part of a current path. One embodiment includes at least one sensing electrode 135, one therapy electrode 140 disposed in front of the subject, e.g., proximate to the subject's chest, and two therapy electrodes 140 disposed in back of the subject, e.g. proximate to the subject's back.

Garment 105 can hold electrodes 135 and 140 in position, for example against the subject's skin around the subject's torso. Clothes or other material may be present between garment 105 and the subject's skin. When positioned against the subject, sensing electrodes 135 can sense electrocardiogram signals used be control unit 130 to monitor the subject's cardiac activity. When control unit 130 identifies an arrhythmia or other cardiac event, therapy electrodes 140, when positioned with a conductive surface facing the subject can deliver defibrillating energy to the subject to convert the arrhythmia to a normal sinus rhythm.

In one embodiment, sensing electrodes 135 and therapy electrodes 140 are securely positioned facing the subject's body in order for sensing electrodes 135 to sense cardiac, respiratory, or other information about the subject; and for therapy electrodes 140 to apply treatment to the subject. For example, sensing electrode 135 can include electrocardiogram electrodes that directly or indirectly (e.g., via clothes, a conductive protective barrier, or a conductive fluid) contact the subject's skin to sense an electrocardiogram signal with minimal artifacts. Further, a conductive surface of therapy electrode 140 can directly or indirectly contact the subject's skin to reduce impedance between therapy electrode 140 and the subject's skin and to efficiently deliver defibrillating energy to the subject, without causing burns, blisters, inflammation, or other damage to the subject's skin. In one embodiment, conductive fluid is released from replaceable receptacles that are disposed in wearable therapeutic device 100 to contact the subject's skin and surfaces of sensing electrode 135 or therapy electrode 140 to reduce impedance and improve the quality of sensed electrocardiogram signals.

In one embodiment wearable therapeutic device 100 includes at least one conductive thread 150. Conductive thread 150 can include a metallic or other conductive material, such as a conductive wire that is configured in a stitched (e.g., zig-zag) pattern. Conductive thread 150 can stretch or expand together with garment 105. Conductive thread 150 may be at least partially shielded, jacketed, or insulated, and may include contact surfaces that are broader than the rest of conductive thread 150 and configured to contact conductive surfaces of sensing electrode 135 or therapy electrode 140. Conductive thread 150 can connect to a power supply of wearable therapeutic device 100 directly or via intervening elements such as conductive element 155 or wires. The power supply can also be associated with external defibrillator 115, control unit 130, alarm module 120, or monitor 125.

Control unit 130 can detect open or closed circuits that include conductive thread 150 and at least one of sensing electrode 135 and therapy electrode 140 to determine that electrode 135 or 140 is improperly positioned, e.g., facing away from the subject, or properly positioned, e.g., facing toward the subject, (or the area the subject occupies when the subject is wearing wearable therapeutic device 100). For example, conductive thread 150 can be located in a lateral side of pocket 160 distal from the subject. When a conductive surface of electrodes 135 or 140 contacts the conductive thread, that conductive surface is facing away from the subject, and in this example is improperly positioned to sense cardiac information or to apply therapy. Control unit 130 can detect this contact, for example by detecting current due to the closed circuit formed by the contact, to determine that electrode 135 or 140 is improperly positioned. In another example, conductive thread 150 can be located in a lateral side of pocket 160 that is proximate to the subject. When a conductive surface of electrodes 135 or 140 contacts the conductive thread, that conductive surface in this example is facing toward the subject, and properly positioned to sense cardiac information or to apply therapy. The formation of this circuit through which current may flow can be identified by control unit 130 to determine that electrode 135 or 140 is properly positioned.

In other examples, when conductive thread 150 is proximate to the subject, e.g., in a lateral side of pocket 160 closest to the subject, an open circuit can indicate that electrodes 135 or 140 are absent or improperly positioned with their conductive surfaces facing away from the subject. When conductive thread 150 is distal to the subject, e.g., in a lateral side of pocket 160 furthest from the subject, an open circuit can indicate that electrodes 135 or 140 are properly positioned with conductive surfaces facing toward the subject, and away from conductive thread 150 in this example.

In one embodiment, garment 105 or its components (e.g., belt 110 or strap 145) include at least one pocket 160 to house at least one electrode (e.g., sensing electrode 135 or therapy electrode 140). At least one pocket 160 can also house control unit 130, external defibrillator 115, alarm module 120, monitor 125, and power supplies and other electronic equipment such as memory storage units. Pocket 160 can have the form of a pouch, sleeve, slit, or flap with an opening on at least one side for entry or removal of sensing electrode 135 or therapy electrode 140. At least one button, snap, or zipper, can secure openings of pocket 160 so that, for example, therapy electrode 140 does not fall out of pocket 160 due to subject movement. In one embodiment, the opening of pocket 160 is not secured by an additional element (e.g., button, snap, hook and loop fastener, fastener, latch, or zipper) and is formed to accommodate sensing electrode 135 or therapy electrode 140. For example, at least part of pocket 160 can have elastic characteristics so that at least a portion expands to accommodate entry of sensing electrode 135 or therapy electrode 140, and contracts to secure any electrode housed in pocket 160.

In one embodiment, pocket 160 has first and second lateral sides, seams around three edges, and a fourth edge open to accommodate entry and removal of sensing electrode 135 or therapy electrode 140 into pocket 160. The seams need not be continuous, and need not be stitched. For example, a series of buttons, hook and loop fasteners, zippers or snaps can attach the first and second lateral sides of pocket 160 to each other. The seams can have openings to accommodate wires or other electrical components connected to sensing electrode 135 or therapy electrode 140 and, for example, control unit 130.

In one embodiment, at least one of the first and second lateral sides of pocket 160 is formed at least in part from a conductive mesh material. For example, the mesh material can be a conductive (e.g., metallic) fabric in a fine grid or mesh pattern included in the lateral side of pocket 160 that is facing the subject. The mesh material can facilitate an electrical connection between sensing electrode 135 or therapy electrode 140 and the subject's skin. In one embodiment, conductive thread 150 is included in at least one lateral side of pocket 160. For example, a first lateral side of pocket 160 that faces away from the subject (when wearing wearable therapeutic device 100) can include conductive thread 150, and a second lateral side that faces toward the subject can include the conductive mesh material. Conductive thread 150 can be included in both lateral sides of pocket 160. In one embodiment, control unit 130 detects electrical connections, (e.g., current) between conductive thread 150 and sensing electrode 135 or therapy electrode 140 to determine proper or improper positioning of electrodes 135, 140.

In one embodiment, prior to sensing cardiac information or applying therapy, a conductive fluid is released from capsules proximate to the mesh fabric. The capsules may be located in or proximate to pocket 160. The conductive fluid can cover at least part of the mesh fabric and the subject's skin, and a conductive surface of sensing electrode 135 or therapy electrode 140 to reduce impedance. This can reduce artifacts in the signal from sensing electrode 135 and causes a more efficient and comfortable application of therapy from therapy electrode 140.

In one embodiment, control unit 130 includes at least one processor as described in commonly owned U.S. patent application Ser. No. 12/833,096, titled "System and Method for Conserving Power in a Medical Device," filed on Jul. 9, 2010, which is incorporated by reference herein in its entirety. The referenced application generally describes a processing architecture configured to conserve energy. Control unit 130 can monitor a subject's condition and control wearable therapeutic device 100 operations. For example, sensing electrode 135 can sense electrical activity of the subject's heart signals. These signals can be displayed as an electrocardiograph on monitor 125. When an arrhythmic event or other form of cardiac distress is detected, alarm module 120 can provide a warning that the subject wearing wearable therapeutic device 100 is in danger of, or is experiencing, for example, cardiac arrest. This warning may be audio, visual, haptic (e.g., vibrating alarm module 120) or combinations thereof. This and other information can be stored in memory units associated with control unit 130 for analysis by a doctor, rescuer, the subject, or a health care provider.

In one embodiment, alarm module 120 provides an alarm that indicates that the subject will receive an electric shock from external defibrillator 115 and at least one therapy electrode 140 when the subject is wearing wearable therapeutic device 100, with therapy electrode 140 disposed proximate to the subject's body. Treatment in the form of an electric shock can be applied to the subject wearing wearable therapeutic device 100 unless the subject takes some action to prevent external defibrillator 115 from applying the shock. For example, alarm module 120 or monitor 125 may include an interface having at least one button or touch screen. In this example, the subject can depress a button. This indicates that the subject is conscious. In this example, the shock will not be applied while the subject depresses the button for a sufficient amount of time, or until control unit 130 determines that the electrical heart activity of the subject, detected for example by sensing electrode 135, has returned to normal. Continuing with this example, if the subject loses consciousness, the subject may release the buttons and external defibrillator 115 can apply a shock via at least one therapy electrode 140.

Alarm module 120 can be part of monitor 125 or a separate element of wearable therapeutic device 100. In one embodiment, alarm module 120 alerts and instructs the subject to take corrective action to position or reposition sensing electrode 135 or therapy electrode 140. In one embodiment, alarm module 120 provides a notification that sensing electrode 135 or therapy electrode 140 is improperly positioned. For example, an improperly positioned conductive surface of electrode 135 or 140 can be facing away from the subject, (e.g., not facing towards or not contacting the subject's skin so that information cannot be sensed or therapy cannot be applied) and can contact conductive thread 150. This improper positioning may be due to the subject, manufacturer, or health care provider accidentally inserting electrode 135 or 140 backwards, with its conductive surface facing away from the subject; or due to movement of the subject while wearing wearable therapeutic device 100. The contact between conductive thread 150 and a conductive surface of sensing electrode 135 or therapy electrode 140 can complete or close an electrical circuit, causing current to follow a path that includes conductive thread 150 and a conductive surface of electrode 135 or 140. Control unit 130 can identify the closed circuit, which indicates an improperly positioned electrode 135 or 140, and instruct alarm module 120 to notify the subject of the improper positioning.

Alarm module 120 can also provide a notification that sensing electrode 135 or therapy electrode 140 is properly positioned. For example, conductive thread 150 can be located between the subject and a conductive surface of sensing electrode 135 or therapy electrode 140. In this example, contact between conductive thread 150 and electrode 135 or 140 indicates that electrodes 135 or 140 are properly positioned, with their conductive surfaces facing toward the subject. Control unit 130 can detect this contact and instruct alarm module 120 to notify the subject of the proper electrode 135, 140 positioning.

Alarm module 120 can instruct the subject to tighten belt 110 to position or reposition sensing electrode 135 or therapy electrode 140. This can reduce, for example, signal interference at sensing electrode 135 by positioning this electrode proximate to the subject's skin, or proximate to a desired portion of the subject's body where a stronger electrocardiogram signal can be sensed. This can also reduce impedance between therapy electrode 140 and the subject, or between a plurality of therapy electrodes 140, allowing for more efficient and effective application of therapy to the subject.

Sensing electrode 135 and therapy electrode 140 can be temporary or permanent components of wearable therapeutic device 100. Electrodes 135 and 140 can be housed anywhere in garment 105. For example, at least one sensing electrode 135 can be integral to garment 105 and disposed in pocket 160 proximate to the subject's chest or abdomen when the subject is wearing wearable therapeutic device 100. At least one therapy electrode 140 can be integral to garment 105 and disposed in pocket 160 proximate to the subject's back when the subject is wearing wearable therapeutic device 100. Sensing electrode 135 and therapy electrode 140 may include conductive surfaces such as a metal plate, foil, mesh, wires, thread, or conductive material in a generally circular, ovoid, or quadrilateral shape.

In one embodiment, sensing electrode 135 and therapy electrode 140 include conductive material woven, sewn, or embroidered into wearable treatment device 100. The conductive material can provide connections between any of electrodes 135 and 140, conductive thread 150, conductive element 155, and a battery powered external defibrillator 115. In one embodiment, sensing electrode 135 senses the subject's electrocardiogram signals and provides the sensed information to control unit 130 or external defibrillator 115.

The conductive material that may form at least part of sensing electrode 135 and therapy electrode 140 can have various patterns to achieve proper electrocardiogram sensing and to administer therapy. In one embodiment, sensing electrode 135 or therapy electrode 140 includes only conductive stitching. Sensing electrode 135 or therapy electrode 140 may also include conductive stitching that holds a metal foil or other conductive component in place in garment 105, so that sensing electrode 135 or therapy electrode 140 includes both conductive thread and a conductive foil.

The conductive material can be sewn into garment 105 (e.g., belt 110) in a zigzag pattern that can stretch as part of garment 105. This stretchable conductive stitching connects sensing electrode 135 and therapy electrode 140 with control unit 130 or other garment 105 components (e.g., external defibrillator 115) in the absence of additional wires. In one embodiment, the conductive material (e.g., conductive wiring) can face toward or away from the subject's skin.

In one embodiment, garment 105 includes breathable fabric, or a material that wicks heat away from the subject's body. This can reduce heat buildup between the subject's skin and sensing electrode 135 or therapy electrode 140. Using conductive stitching for electrodes 135 or 140 reduces heat buildup in one embodiment when electrodes 135 or 140 are formed from stitched conductive material in the absence of any further metallic or conductive foil. In one embodiment, sensing electrode 135 or therapy electrode 140 are made of perforated conductive materials that allow air flow proximate to the subject's skin. This air flow can dry sweat or other fluid from the skin to avoid rashes and other skin problems as a result of heat buildup and irritation.

Garment 105 can be adjusted to snugly fit the subject. For example, portions of garment 105 that include sensing electrode 135 and therapy electrode 140 can be substantially flush against the subject, e.g., electrodes 135 and 140 remain substantially in a fixed position against the subject when the subject is moving about as part of a daily routine, or undertaking moderate physical activity. Clothing may be present between garment 105 and the subject. Alarm module 120 can alert the subject when wearable therapeutic device 100 is not sufficiently tight and snug about the subject. For example, alarm module 120 can notify the subject when the portion of garment 105 (e.g., pocket 160) that includes sensing electrode 135 or therapy electrode 140 is not flush with or fairly tightly pressed against the patient in a substantially fixed position.

Garment 105 or its components such as belt 110 or strap 145 can expand or stretch with time or repeated use, which can loosen the fit and positioning of sensing electrode 135 and therapy electrode 140 proximate to the subject. Further, the subject's respiration will typically result in periodic expansion of garment 105. Control unit 130 can detect this expansion and where appropriate, instruct the subject to reposition sensing electrode 135 or therapy electrode 140, for example by tightening garment 105.

Wearable therapeutic device 100 can include at least one conductive element 155, located for example in garment 105, belt 110, or strap 145. In one embodiment, conductive element 155 connects conductive thread 150 with control unit 130. For example, conductive element 155 can be part of the circuit formed when conductive thread 150 and a conductive surface of sensing electrode 135 or therapy electrode 140 make electrical contact with one another. In one embodiment, a connector such as a snap or male-female connector makes the connection between conductive element 155 and conductive thread 150.

Figure 2:
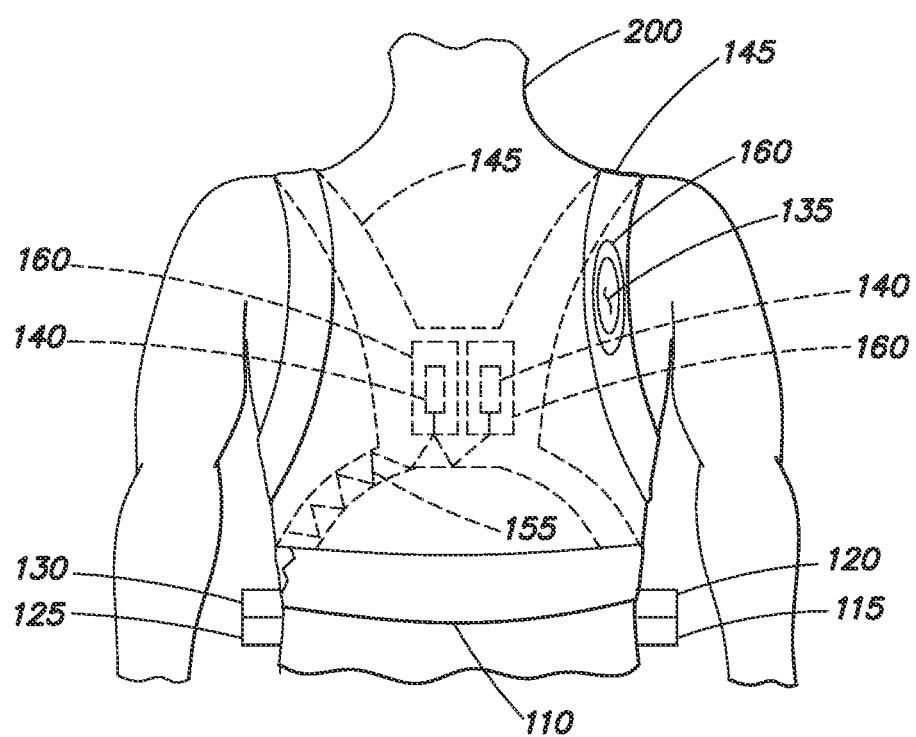
FIG. 2 is a schematic diagram depicting a wearable therapeutic device in accordance with an embodiment.

FIG. 2 is a schematic diagram depicting wearable therapeutic device 100 in accordance with an embodiment. In the example of FIG. 2, garment 105 includes two pockets 160 proximate to the back of subject 200. Each of these pockets 160 includes one therapy electrode 140. While not directly illustrated in FIG. 2, pockets 160 can include conductive thread 150, for example sewn into the inner lateral side of pocket 160 nearest to subject 200, or the outer lateral side of pocket 160, farthest from subject 200. Sensing electrode 135 is also disposed in pocket 160 proximate to the chest of subject 200, in the general vicinity of the heart. Conductive element 155 connects control unit 130 with therapy electrodes 140. Wearable therapeutic device 100 can include more than one conductive element 155. For example, the same or a second conductive element 155 can connect control unit 130 with at least one sensing electrode 135. Wearable therapeutic device 100 can include other elements not illustrated in FIG. 2, such as power supplies, additional electrodes, and additional straps across the chest of subject 200 that can include conductive element 155. In one embodiment, at least one therapy electrode 140 is located in a pocket 160 in front of subject 200, proximate to the chest.

In one embodiment, control unit 130 determines the orientation of sensing electrodes 135 or therapy electrodes 140 to determine if they are properly positioned with a conductive surface of electrodes 135, 140 facing toward subject 200 or improperly positioned with a conductive surface of electrodes 135, 140 facing away from subject 200. Control unit 130 can instruct alarm module 120 to provide a notification to subject 200. The notification can instruct subject 200 to position or reposition sensing electrode 135 or therapy electrode 140. The notification can also indicate that an arrhythmic cardiac event has been detected, based on information from sensing electrode 135, and provide a warning that therapy has been or will be applied within a time period of, for example, a few seconds.

Figure 3:
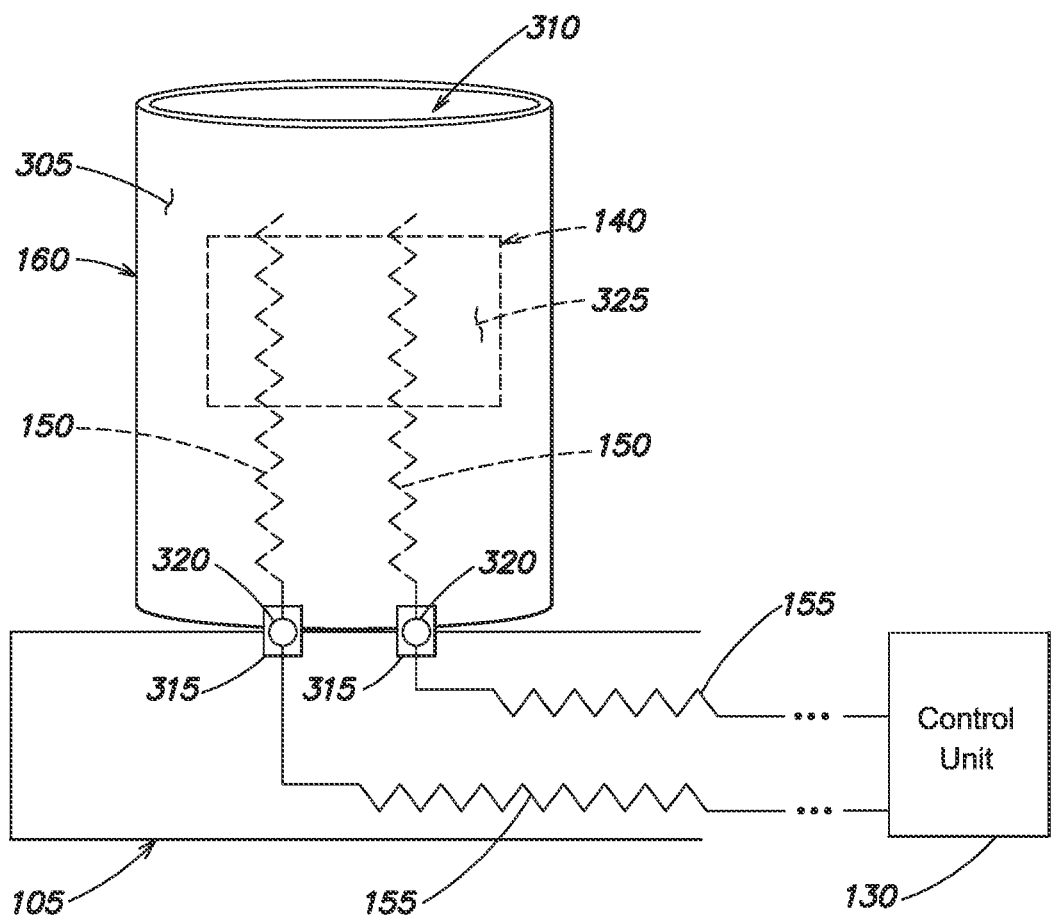
FIG. 3 is a diagram depicting a portion of a wearable therapeutic device with conductive thread sewn into a pocket in accordance with an embodiment.

FIG. 3 depicts a portion of garment 105 where pocket 160 includes conductive thread 150 in accordance with an embodiment. With reference to FIG. 3, conductive thread 150 can be sewn into the fabric of lateral side 305 of pocket 160. Lateral side 305 can be the interior lateral side of pocket 160 that faces inward toward the subject when the subject is wearing wearable therapeutic device 100, or can be the exterior lateral side of pocket 160 that faces outward away from the subject when the subject is wearing wearable therapeutic device 100. In one embodiment, the second lateral side of pocket 160, not visible in FIG. 3, includes a conductive mesh that lowers impedance of the electrical connection between, for example, therapy electrode 140 and the subject.

In one embodiment, opening 310 of pocket 160 receives sensing electrode 135 or therapy electrode 140. One or more flaps, buttons, snaps, fasteners, latches, hook and loop fasteners, or zippers may close opening 310 when electrode 135 or 140 is disposed in pocket 160. Electrodes 135 or 140 can be removed from pocket 160 to be replaced, recharged, repaired, or repositioned. One or more connectors 315 such as conductive snaps 320 can couple conductive thread 150 with conductive element 155. Control unit 130 can receive as input information from conductive element 155 to determine that conductive thread 150 is or is not in contact with a conductive surface of electrode 135 or 140.

At least one therapy electrode 140 can be disposed in pocket 160, as depicted in FIG. 3. Sensing electrodes 135 may also be disposed in pockets 160. In one embodiment, conductive surface 325 of therapy electrode 140 contacts conductive thread 150 sewn into lateral side 305 of pocket 160. Control unit 130 can determine that this contact has been made, for example by sensing current in conductive element 155, to identify the direction in which conductive surface 325 is facing, e.g., inward toward the subject or outward away from the subject. Control unit 130 can then instruct therapy electrode 140 and defibrillator 115 to apply treatment (e.g., when therapy electrode 140 is properly positioned) or to withhold treatment (e.g., when therapy electrode 140 is improperly positioned). Control unit 130 with alarm module 120 or monitor 125 can also notify the subject of proper of improper positioning, or instruct the subject to reposition therapy electrode 140 or garment 105.

Figure 4:
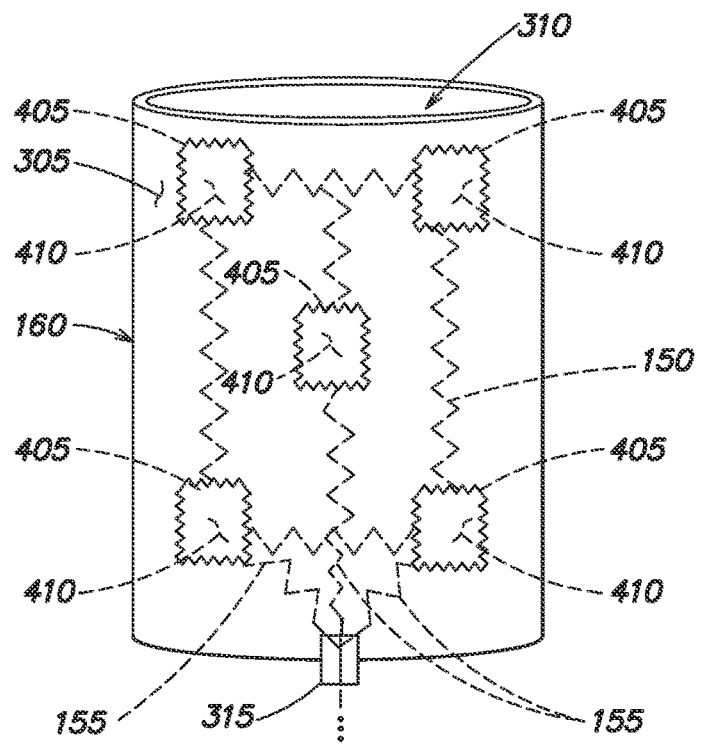
FIG. 4 is a diagram depicting a portion of a wearable therapeutic device with conductive thread sewn into a pocket in accordance with an embodiment.

FIG. 4 depicts a portion of garment 105 where pocket 160 includes conductive thread 150 in accordance with an embodiment. Conductive thread 150 can form various patterns in lateral side wall 305 of pocket 160. For example, conductive thread 150 can be woven into the fabric of pocket 160 to form a series of lines, each line substantially parallel to an edge of lateral side 305, with a conductive patch 405 disposed in each of the four corners of lateral side 305. An additional conductive patch 405 may be located substantially in the center of lateral side 305, with conductive thread 150 connecting the central conductive patch 405 with the rest of the pattern. Conductive patches 405 can include conductive thread 150 around their edges, with central portion 410 being made of the same material as the rest of lateral side wall 305, or central portion 410 can include conductive material, such as a mesh, connected to conductive thread 150. One or more conductive elements 155 can connect with conductive thread 150 at one or at a plurality of different points of conductive thread 150, such as at one or more conductive patches 405, or at the corner areas of lateral side wall 305. In one embodiment, a plurality of conductive elements 155 connects with a plurality of conductive threads 150 at lateral side 305.

Figure 5:
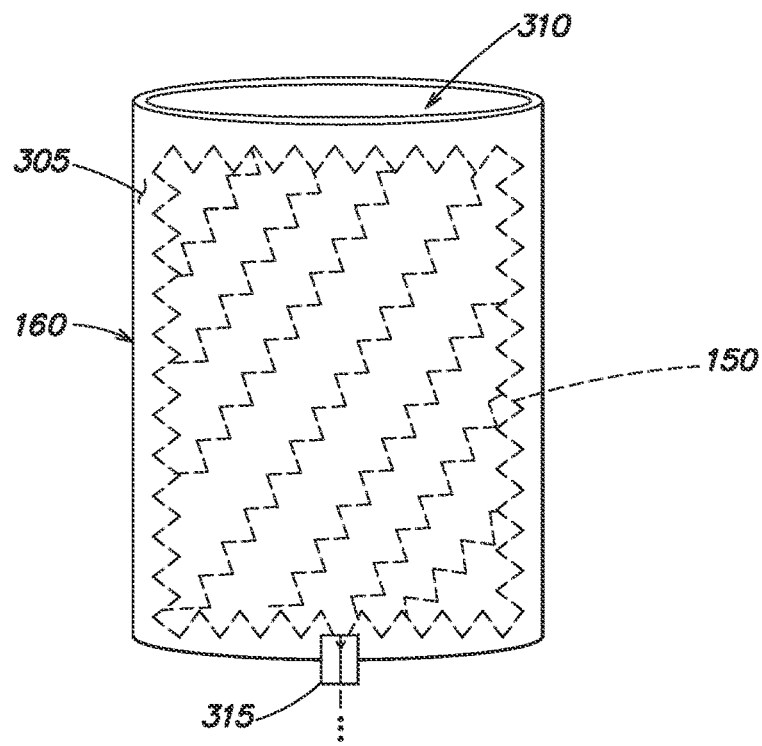
FIG. 5 is a diagram depicting a portion of a wearable therapeutic device with conductive thread sewn into a pocket in accordance with an embodiment.

FIG. 5 depicts a portion of garment 105 where pocket 160 includes conductive thread 150 in accordance with an embodiment. Conductive thread 150 can be woven around the edges of lateral side 305 with a plurality of substantially parallel lines of conductive thread 150 running diagonally across lateral side 305. The substantially parallel lines may or may not be evenly spaced. Other configurations are possible. For example, conductive thread 150 may form serpentine, circular, oval, quadrilateral, coiled, or triangular shapes on lateral side 305. In one embodiment, conductive thread 150 is woven into lateral side 305 sufficiently spaced so that conductive surface 325 contacts conductive thread 150 when sensing electrode 135 or therapy electrode 140 is disposed in pocket 160 with conductive surface 325 facing lateral side 305. Conductive elements 155 can connect with conductive thread 150 at multiple points of conductive thread 150.

Figure 6:
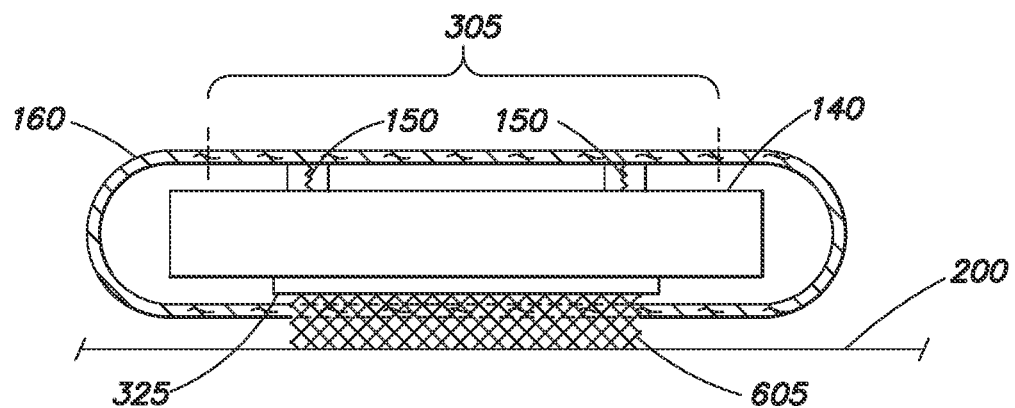
FIG. 6 is a cross sectional view of a wearable therapeutic device with an electrode disposed in a pocket of the wearable therapeutic device in accordance with an embodiment.

FIG. 6 depicts a cross sectional view of garment 105 with therapy electrode 140 disposed in pocket 160. Conductive surface 325 is facing toward conductive mesh 605 and subject 200, away from conductive thread 150, and in this example is properly positioned to apply treatment to subject 200 because conductive surface 325 is in contact with subject 200 via conductive mesh 605. Intervening elements such as conductive fluid or clothes can be present. Conductive thread 150 is woven into lateral side 305 of pocket 160 and not in electrical contact with conductive surface 325. In one embodiment, control unit 130 can determine that therapy electrode 140 is properly positioned in pocket 160 based on the absence of an electrical connection between conductive surface 325 and conductive thread 150. In one embodiment, sensing electrodes are disposed in pocket 160.

In one embodiment, sensing electrode 135 or therapy electrode 140 includes a plurality of conductive surfaces 325. For example, rather than a single continuous conductive surface 325, therapy electrode 140 can have two separate conductive surfaces 325 with an insulating or non-conductive gap between them. In this example, a closed circuit forms when conductive thread 150 bridges the gap and contacts each of the two (or other plurality) of conductive surfaces 325. Control unit 130 can determine that therapy electrode 140 is improperly positioned in pocket 160 based on the electrical connection between both conductive surfaces 325 and conductive thread 150, or that therapy electrode 140 is properly positioned in pocket 160 based on an absence of an electrical connection.

Figure 7:
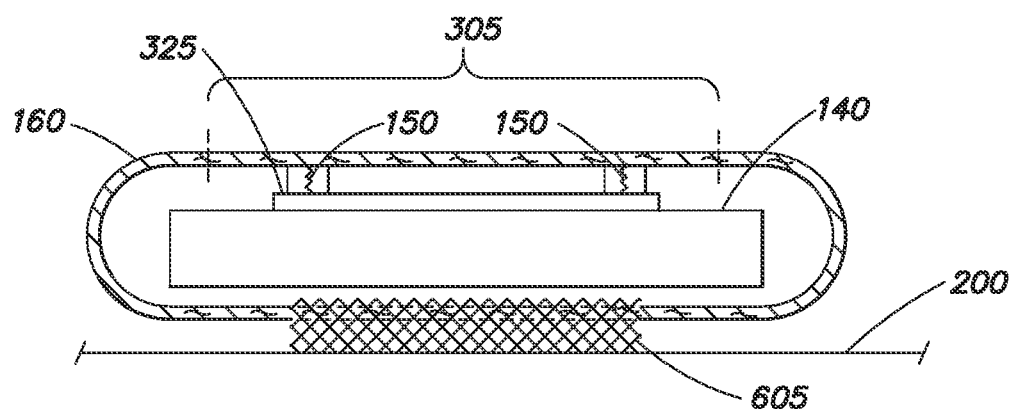
FIG. 7 is a cross sectional view of a wearable therapeutic device with an electrode disposed in a pocket of the wearable therapeutic device in accordance with an embodiment.

FIG. 7 depicts a cross sectional view of garment 105 with therapy electrode 140 disposed in pocket 160. Conductive surface 325 is facing toward conductive thread 150, away from conductive mesh 605 and subject 200, and in this example is improperly positioned to apply treatment to the subject because conductive surface 325 is not directly or indirectly in contact with subject 200. Conductive thread 150 is woven into lateral side 305 of pocket 160 and is in electrical contact with conductive surface 325. In one embodiment, control unit 130 can detect this electrical connection and based on this connection determine that therapy electrode 140 is improperly positioned in pocket 160. It should be appreciated that the therapy electrode 140 could have a plurality of conductive surfaces 325 separated by an insulating or non-conductive gap, with the presence of an electrical connection between the conductive surfaces 325 (due to the presence of the conductive thread) being indicative of improper positioning. In one embodiment, sensing electrodes may also be disposed in a pocket similar to that of pocket 160.

In one embodiment, surfaces of pocket 160 can include a pressure sensor such as a spring loaded sensor or piezoelectric sensor to detect contact with conductive thread 150, as an alternative or complement to conductive surface 325. Sensing electrodes 135 and therapy electrodes 140 can also include pressure sensors to detect contact with surfaces of pocket 160. These pressure sensors can include conductive elements to detect electrical connections with garment 105 components such as conductive surface 325 or conductive thread 150. These pressure sensors can also determine that garment 105 is properly fitted on the subject with the appropriate amount of tension to hold garment components such as therapy electrodes 140 in position suitable to deliver treatment to the subject.

Figure 8:
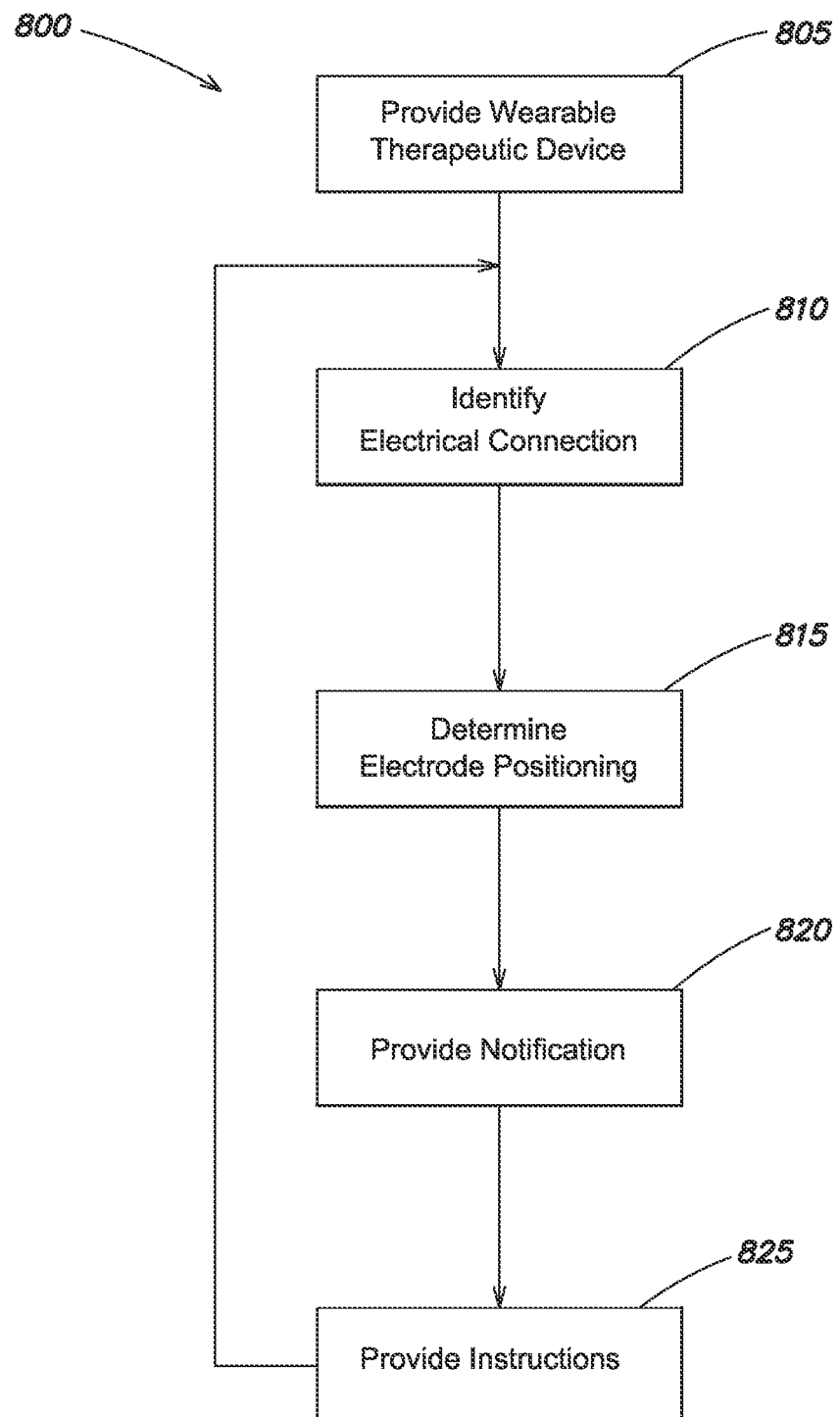
FIG. 8 is a flowchart depicting a method of facilitating care of a subject in accordance with an embodiment.

FIG. 8 is a flowchart depicting a method 800 of facilitating care of a subject. In one embodiment, method 800 includes an act of providing a wearable therapeutic device (ACT 805). In one embodiment, providing the wearable therapeutic device (ACT 805) includes providing a device that includes at least one electrode, such as a therapy electrode or sensing electrode, and at least one length of conductive thread. The electrode may be housed in a garment of the wearable therapeutic device, and providing the wearable therapeutic device (ACT 805) may include providing a device with the conductive thread included in at least part of the garment, such as a lateral side of a pocket where the electrode is included.

Providing the wearable therapeutic device (ACT 805) may also include providing a device having a control unit configured to identify electrical connections between conductive surfaces of electrodes and conductive thread, to determine, based on the identified connections or lack thereof, positioning of an electrode, and to notify the subject of proper or improper electrode positioning. Providing the wearable therapeutic device (ACT 805) may also include providing a device with an alarm module coupled with a control unit to notify the subject of events, conditions, or information about the subject's condition or about the condition of the wearable therapeutic device, including positioning of its components.

Method 800 can include an act of identifying an electrical connection (ACT 810). In one embodiment, this includes identifying an electrical connection between a conductive surface of the therapy electrode and the conductive thread. For example, contact between the conductive surface and the conductive thread may form a circuit, and a control unit can sense current that follows a path between the conductive surface and the conductive thread to identify (ACT 810) an electrical connection between these components. Other elements can be included in the circuit, such as a conductive element, e.g., a wire that connects the conductive thread with, for example, a power supply or control unit.

Method 800 can include an act of determining electrode positioning (ACT 815). In one embodiment, determining electrode positioning (ACT 815) is based on the identified electrical connection (ACT 810). For example, when the conductive thread is woven into a lateral side pocket distal from a subject, or distal from the area that a subject occupies when the subject is wearing the device, electrode positioning can be determined (ACT 815) to be improperly facing away from the subject when an electrical connection is identified (ACT 810).

In one embodiment, electrode positioning can be determined (ACT 815) to be proper when an electrical connection is not identified (ACT 810). For example, an open circuit can be detected, the open circuit including at least portions of the conductive surface of the electrode and the conductive thread. When the conductive thread is located between the subject and the conductive surface of the electrode, the electrode can be determined (ACT 815) to be properly positioned when there is contact between the conductive surface of the electrode and the conductive thread.

Method 800 may include an act of providing a notification (ACT 820). In one embodiment, an alarm module provides notification (ACT 820) that an electrode is properly or improperly positioned. The notification may be provided (ACT 820) audibly, visually, or haptically by an alarm module included in the wearable therapeutic device. The notification can be provided (ACT 820) to the subject wearing the device or to a health care provider remote from the subject via a network connection. In one embodiment, providing the notification (ACT 820) includes providing instructions to adjust positioning of an electrode. For example, notification can be provided (ACT 820) that an electrode is improperly positioned in a pocket of the device, and the notification can include instructions to position the electrode with its conductive surface facing inward, toward the subject. In one embodiment, providing a notification (ACT 820) confirms proper placement of an electrode. Notification can also be provided indicating that a cardiac event or other information has been sensed by a sensing electrode, that therapy will be applied by a treatment electrode, or that therapy has been applied by a treatment electrode. In one embodiment, providing a notification (ACT 820) alerts bystanders or health care providers to stay away from and not touch the subject due to past application of therapy (e.g., a defibrillation shock) or imminent future application of therapy.

In one embodiment, method 800 includes an act of providing instructions (ACT 825). For example, providing instructions (ACT 825) can include providing instructions to operate the wearable therapeutic device, or providing instructions on how to wear the wearable therapeutic device. In one embodiment, the instructions include instructions to the subject regarding positioning of wearable therapeutic device components, such as sensing or therapy electrodes. For example, due to an identified (ACT 810) electrical connection between an electrode and conductive thread of the garment, instructions can be provided (ACT 825) to the subject to position an electrode proximate to an area of the subject's body, such as the center of the back, or proximate to the chest and heart of the subject, so that the electrodes are positioned to provide therapy to the subject or to sense cardiac or respiratory function of the subject.

Having now described some illustrative embodiments, it is apparent that the foregoing is illustrative and not limiting, having been presented by way of example. In particular, although many of the examples presented herein involve specific combinations of method acts or system elements, it is understood that those acts and those elements may be combined in other ways to accomplish the same objectives. Acts, elements and features discussed only in connection with one embodiment are not intended to be excluded from a similar role in other embodiments.

Note that in FIGS. 1 through 8, the enumerated items are shown as individual elements. In actual implementations of the systems and methods described herein, however, they may be inseparable components of other electronic devices such as a digital computer. Thus, actions described above may be implemented at least in part in software that may be embodied in an article of manufacture that includes a program storage medium. In one embodiment, the program storage medium is non-transitory. The program storage medium includes data signals embodied in one or more of a carrier wave, a computer disk (magnetic, or optical (e.g., CD or DVD, or both)), non-volatile memory, tape, a system memory, and a computer hard drive.

From the foregoing, it is appreciated that embodiments of the wearable therapeutic device described herein afford an effective way to verify proper electrode positioning. The wearable therapeutic device according to various embodiments is able to determine electrode positioning based on electrical connections between the electrode and conductive thread woven into the garment so that information may be sensed accurately and so that therapy may be applied when appropriate. This increases efficiency and effectiveness of the wearable therapeutic device.

Any references to front and back, left and right, top and bottom, inner and outer, toward and away, or upper and lower and the like are intended for convenience of description, not to limit the present systems and methods or their components to any one positional or spatial orientation.

Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements to single or plural configurations. References to any act or element being based on any information, act or element may include embodiments where the act or element is based at least in part on any information, act, or element.

Any embodiment disclosed herein may be combined with any other embodiment, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. Such terms as used herein are not necessarily all referring to the same embodiment. Any embodiment may be combined with any other embodiment in any manner consistent with the aspects and embodiments disclosed herein.

References to "or" may be construed as inclusive so that any terms described using "or" may indicate any of a single, more than one, and all of the described terms. Intervening embodiments, acts, or elements are not essential unless recited as such.

Where technical features in the drawings, detailed description or any claim are followed by reference signs, the reference signs have been included for the sole purpose of increasing the intelligibility of the drawings, detailed description, and claims. Accordingly, neither the reference signs nor their absence have any limiting effect on the scope of any claim elements.

One skilled in the art will realize the systems and methods described herein may be embodied in other specific forms without departing from the characteristics thereof. For example, references to electrodes facing toward or away from the subject include references to where the subject would be positioned when wearing the wearable therapeutic device. Electrode positioning can be determined in the absence of the subject wearing the device. Further, conductive thread, conductive elements, electrodes, and other components can be at least partially insulated, jacketed, or sleeved. Electrode positioning can be determined to be proper or improper based on detection of electrical connections or the absence of electrical connections. For example, either an electrical connection indicating an outward facing electrode, or the absence of an electrical connection indicating an inward facing electrode, can indicate an improperly positioned electrode. In some embodiments, an electrical connection indicating an inward facing electrode, or the absence of an electrical connection indicating an outward facing electrode, can indicate a properly positioned electrode. The foregoing embodiments are illustrative rather than limiting. Scope of the systems and methods described herein is thus indicated by the appended claims, rather than the foregoing description, and changes that come within the meaning and range of equivalency of the claims are embraced therein.

What is claimed is:

1. A wearable defibrillator for instructing proper electrode positioning, comprising:
   a garment comprising
      a belt configured to secure the garment about a torso of a subject;
      a therapy electrode pocket;
      a conductive mesh included in at least one side of the therapy electrode pocket; and
      at least one fastener configured to secure an opening of the therapy electrode pocket;
   a therapy electrode having a conductive surface, the therapy electrode configured to be disposed within the therapy electrode pocket;
      wherein the conductive mesh of the garment is configured to facilitate an electrical connection between the therapy electrode and the subject's skin;
   a monitor configured to audibly, visually or haptically notify the subject of improper positioning of the therapy electrode; and
   a control unit comprising at least one processor configured to
      determine whether the conductive surface of the therapy electrode is properly positioned in the therapy electrode pocket with the conductive surface of the therapy electrode facing towards the subject to apply therapy to the subject,
      cause, responsive to determining that the conductive surface of the therapy electrode is not properly positioned with the conductive surface of the therapy electrode facing towards the subject so as to apply the therapy to the subject, the monitor to notify the subject of improper positioning of the therapy electrode, and
      cause the monitor to instruct the subject to at least one of tighten the garment or reposition the therapy electrode so that the conductive surface of the therapy electrode is positioned with the conductive surface of the therapy electrode facing towards the subject to apply the therapy to the subject.

2. The wearable defibrillator of claim 1, wherein the pocket comprises a first lateral side proximate to the subject and a second lateral side distal to the subject, and wherein the first lateral side of the pocket includes the conductive mesh.

3. The wearable defibrillator of claim 2, wherein the at least one fastener comprises at least one button, snap, or zipper.

4. The wearable defibrillator of claim 3, further comprising at least one electrocardiogram (ECG) sensing electrode configured to sense ECG activity of the subject's heart.

5. The wearable defibrillator of claim 4, wherein the at least one ECG sensing electrode includes a plurality of ECG sensing electrodes.

6. The wearable defibrillator of claim 1, wherein the at least one fastener comprises at least one button, snap, or zipper.

7. The wearable defibrillator of claim 1, further comprising at least one electrocardiogram (ECG) sensing electrode configured to sense ECG activity of the subject's heart.

8. The wearable defibrillator of claim 7, wherein the at least one ECG sensing electrode includes a plurality of ECG sensing electrodes.

9. The wearable defibrillator of claim 1, wherein the monitor is further configured to audibly, visually, or haptically notify the subject of proper positioning of the therapy electrode.

10. The wearable defibrillator of claim 1, wherein the pocket comprises one of a pouch, a sleeve, a slit, or a flap.

11. The wearable defibrillator of claim 1, wherein the monitor comprises an interface having at least one button or touch screen for user input.

12. The wearable defibrillator of claim 1, wherein the at least one processor is further configured to monitor for an arrhythmia condition based on sensed electrocardiogram (ECG) activity of the subject's heart.

13. The wearable defibrillator of claim 12, wherein the monitor is further configured to cause a warning that the therapy will be applied to the subject on detecting the arrhythmia condition.

14. The wearable defibrillator of claim 12, wherein the monitor comprises an interface having at least one button or touch screen for user input.

15. The wearable defibrillator of claim 1, wherein the at least one processor is further configured to cause the therapy to not be applied to the subject if the subject provides the user input.

16. The wearable defibrillator of claim 1, further comprising a plurality of electrocardiogram (ECG) sensing electrodes permanently integrated into the garment, the plurality of ECG sensing electrodes configured to sense ECG activity of the subject's heart.

17. The wearable defibrillator of claim 16, wherein the at least one processor is further configured to monitor for an arrhythmia condition based on the sensed ECG activity of the subject's heart.

18. The wearable defibrillator of claim 17, wherein the monitor is further configured to cause a warning that the therapy will be applied to the subject on detecting the arrhythmia condition.

19. The wearable defibrillator of claim 18, wherein the monitor comprises an interface having at least one button or touch screen for user input.

20. The wearable defibrillator of claim 19, wherein the at least one processor is further configured to cause the therapy to not be applied to the subject if the subject provides the user input.

* * * * *